United States Patent
Wagner et al.

(10) Patent No.: US 10,737,210 B2
(45) Date of Patent: Aug. 11, 2020

(54) FILTER PRECLEANER

(71) Applicant: Cummins Filtration IP, Inc., Columbus, IN (US)

(72) Inventors: Brian K. Wagner, Stoughton, WI (US); Anil I. Sawant, Pune (IN); Madhuri S. Gawali, Maharashtra (IN)

(73) Assignee: CUMMINS FILTRATION IP, INC, Columbus, IN (US)

( * ) Notice: Subject to any disclaimer, the term of this patent is extended or adjusted under 35 U.S.C. 154(b) by 213 days.

(21) Appl. No.: 15/753,721

(22) PCT Filed: Aug. 23, 2016

(86) PCT No.: PCT/US2016/048142
§ 371 (c)(1),
(2) Date: Feb. 20, 2018

(87) PCT Pub. No.: WO2017/035123
PCT Pub. Date: Mar. 2, 2017

(65) Prior Publication Data
US 2018/0264387 A1    Sep. 20, 2018

Related U.S. Application Data

(60) Provisional application No. 62/209,689, filed on Aug. 25, 2015.

(51) Int. Cl.
*B01D 47/00* (2006.01)
*B01D 46/00* (2006.01)
(Continued)

(52) U.S. Cl.
CPC ......... *B01D 46/0031* (2013.01); *B01D 45/06* (2013.01); *B01D 45/08* (2013.01);
(Continued)

(58) Field of Classification Search
CPC ........... B01D 46/0031; B01D 46/2411; B01D 51/00; B01D 45/06; B01D 45/08;
(Continued)

(56) References Cited

U.S. PATENT DOCUMENTS 2,801,751 A * 8/1957 Thomas ............... B01D 35/147
210/133
3,199,526 A * 8/1965 Pall ........................... F16T 1/24
137/192

(Continued)

FOREIGN PATENT DOCUMENTS

| CN | 2850693 | 12/2006 |
|---|---|---|
| CN | 102105206 | 6/2011 |
| CN | 103826718 | 5/2014 |

OTHER PUBLICATIONS

International Search Report and Written Opinion issued for PCT Application No. PCT/US2016/048142, dated Nov. 10, 2016, 15 pages.

(Continued)

*Primary Examiner* — Dung H Bui
(74) *Attorney, Agent, or Firm* — Foley & Lardner LLP (57) ABSTRACT

A filter precleaner for precleaning an unfiltered gaseous mixture. A coalescing filter includes a filter media for filtering a gas, a nozzle assembly for precleaning an unfiltered gaseous mixture, and a lower endplate. The nozzle assembly includes a first nozzle plate positioned upstream of the filter media. The lower endplate is positioned at a lower end of the filter media beneath the first nozzle plate. The lower endplate allows liquid to drain through the lower endplate. The unfiltered gaseous mixture impacts the lower endplate such that liquid from the unfiltered gaseous mixture flows through the lower endplate and gas from the unfiltered gaseous mixture flows through the filter media.

25 Claims, 7 Drawing Sheets

(51) Int. Cl.
*B01D 45/06* (2006.01)
*B01D 45/08* (2006.01)
*B01D 50/00* (2006.01)
*B01D 46/24* (2006.01)
*B01D 51/00* (2006.01)
*A61K 31/167* (2006.01)
*A61K 31/485* (2006.01)
*F01M 13/04* (2006.01)

(52) U.S. Cl.
CPC ........ *B01D 46/2411* (2013.01); *B01D 50/002* (2013.01); *B01D 51/00* (2013.01); *A61K 31/167* (2013.01); *A61K 31/485* (2013.01); *A61K 2300/00* (2013.01); *F01M 13/04* (2013.01)

(58) Field of Classification Search
CPC ............. B01D 50/002; A61K 2300/00; A61K 31/167; A61K 31/485; F01M 13/04
See application file for complete search history.

(56) References Cited

U.S. PATENT DOCUMENTS

| | | | | |
|---|---|---|---|---|
| 4,136,009 A * | 1/1979 | Samiran | ............ | B01D 17/0214 210/114 |
| 4,336,043 A * | 6/1982 | Aonuma | ............ | B01D 46/0012 210/259 |
| 4,419,113 A * | 12/1983 | Smith | ............ | B01D 46/0021 422/562 |
| 4,516,994 A * | 5/1985 | Kocher | ............ | B01D 45/12 210/304 |
| 4,913,712 A * | 4/1990 | Gabathuler | ............ | F01N 3/0211 55/482 |
| 5,246,472 A * | 9/1993 | Herman | ............ | B01D 46/2411 55/429 |
| 5,288,469 A * | 2/1994 | Skalla | ............ | A61B 18/00 261/DIG. 26 |
| 5,548,893 A * | 8/1996 | Koelfgen | ............ | B01D 29/15 29/888.011 |
| 5,571,298 A * | 11/1996 | Buck | ............ | B01D 39/12 422/174 |
| 5,606,854 A * | 3/1997 | Hoffmann | ............ | F01N 3/0211 55/463 |
| 5,779,900 A * | 7/1998 | Holm | ............ | B01D 29/15 210/411 |
| 5,800,597 A | 9/1998 | Perrotta et al. | | |
| 6,085,915 A * | 7/2000 | Schwandt | ............ | B01D 29/21 210/411 |
| 6,290,738 B1 | 9/2001 | Holm | | |
| 6,627,078 B1 * | 9/2003 | Wagner | ............ | B01D 29/21 210/238 |
| 7,320,723 B2 * | 1/2008 | Sewell, Sr. | ............ | B01D 53/0415 55/385.3 |
| 7,857,883 B2 | 12/2010 | Scheckel et al. | | |
| 8,029,592 B2 * | 10/2011 | Schramm | ............ | B01D 39/2068 422/177 |
| 8,152,884 B1 * | 4/2012 | Severance | ............ | B01D 45/08 55/462 |
| 8,404,014 B2 * | 3/2013 | Israel | ............ | B01D 39/1623 55/385.3 |
| 9,260,993 B1 * | 2/2016 | Mainiero | ............ | B01D 45/08 |
| 10,464,005 B2 * | 11/2019 | Tanaka | ............ | B01D 46/2414 |
| 2002/0088212 A1 * | 7/2002 | Ernst | ............ | B01D 45/02 55/385.3 |
| 2005/0211232 A1 * | 9/2005 | Dushek | ............ | F01M 13/0011 123/574 |
| 2007/0186526 A1 * | 8/2007 | Lane | ............ | B01D 46/0031 55/486 |
| 2009/0050121 A1 | 2/2009 | Holzmann et al. | | |
| 2009/0120854 A1 * | 5/2009 | Parikh | ............ | B01D 45/08 210/137 |
| 2011/0315018 A1 * | 12/2011 | Moens | ............ | B01D 46/0004 96/400 |
| 2012/0267294 A1 * | 10/2012 | Herman | ............ | B01D 29/232 210/137 |
| 2013/0056409 A1 * | 3/2013 | Sawant | ............ | B01D 35/30 210/442 |
| 2013/0062291 A1 | 3/2013 | Hackett et al. | | |
| 2013/0167816 A1 * | 7/2013 | Dawar | ............ | F02M 25/06 123/573 |
| 2014/0165977 A1 | 6/2014 | Copley et al. | | |
| 2015/0352474 A1 * | 12/2015 | Hawkins | ............ | B01D 35/30 210/450 |
| 2016/0011037 A1 * | 1/2016 | Sugio | ............ | B01D 45/08 96/417 |

OTHER PUBLICATIONS

First Office Action issued for Chinese Patent Application No. 2016800444071, dated May 24, 20196, including translation, 13 pages.
First Office Action issued for Indian Patent Application No. 201847002153, dated May 29, 2020, 6 pages.

* cited by examiner

(12) United States Patent
US 10,737,210 B2

FILTER PRECLEANER

CROSS-REFERENCE TO RELATED PATENT APPLICATIONS

The application is a National Stage of PCT Application No. PCT/US2016/048142, filed Aug. 23, 2016, which, claims priority to and the benefit of U.S. Provisional Patent Application No. 62/209,689, filed on Aug. 25, 2015. The contents of both applications are incorporated herein by reference in their entirety and for all purposes.

FIELD

The present application relates to filter precleaners for precleaning an unfiltered gaseous mixture.

BACKGROUND

Gas filters, such as coalescing gas filters, may include a filter element that the unfiltered fluid may flow through for filtration. However, particularly in with gas filtration, any liquid in the unfiltered air or gaseous mixture (e.g., aerosol) may be directed with the gas into the filter media. This excess liquid may decrease the life and overall efficiency of the filter media.

SUMMARY

Various embodiments provide for a coalescing filter that includes a filter media, a nozzle assembly for precleaning an unfiltered gaseous mixture, and a lower endplate. The nozzle assembly includes a first nozzle plate positioned upstream of the filter media. The lower endplate is positioned at a lower end of the filter media beneath the first nozzle plate. The lower endplate allows liquid to drain through the lower endplate. The unfiltered gaseous mixture impacts the lower endplate such that liquid from the unfiltered gaseous mixture flows through the lower endplate and gas from the unfiltered gaseous mixture flows through the filter media.

Further embodiments provide for a filter assembly that includes a filter housing and a coalescing filter positioned within the filter housing. The coalescing filter includes a filter media, a nozzle assembly for precleaning an unfiltered gaseous mixture, and a lower endplate. The nozzle assembly includes a first nozzle plate positioned upstream of the filter media. The lower endplate is positioned at a lower end of the filter media beneath the first nozzle plate. The lower endplate allows liquid to drain through the lower endplate. The unfiltered gaseous mixture impacts the lower endplate such that liquid from the unfiltered gaseous mixture flows through the lower endplate and gas from the unfiltered gaseous mixture flows through the filter media.

Even further embodiments provide for a method of precleaning an unfiltered gaseous mixture. The method includes directing the unfiltered gaseous mixture into a filter assembly, directing the unfiltered gaseous mixture through a first nozzle plate of a nozzle assembly of the filter assembly, impacting the unfiltered gaseous mixture on a lower endplate, and draining liquid from the unfiltered gaseous mixture through the lower endplate. The first nozzle plate is positioned upstream of a filter media for filtering a gas. The lower endplate is positioned at a lower end of the filter media beneath the first nozzle plate. Gas from the unfiltered gaseous mixture flows through the filter media.

These and other features (including, but not limited to, retaining features and/or viewing features), together with the organization and manner of operation thereof, will become apparent from the following detailed description when taken in conjunction with the accompanying drawings, wherein like elements have like numerals throughout the several drawings described below.

DETAILED DESCRIPTION

Referring to the figures generally, the various embodiments disclosed herein relate to a filter precleaner with a drain. More specifically, the precleaner described herein may be used with a filter assembly and may increase the life and improve the overall efficiency of filter media in the filter assembly.

Referring to FIGS. 1A-1D, there is shown a filter assembly 20 that includes an internal filter precleaner or nozzle assembly 50, according to one embodiment. With the assistance of the precleaner, the filter assembly 20 may filter a variety of different gases, including gas with liquids, dry gas, gas with aerosol, natural gas, or gaseous fuel. According to one embodiment, the gas is air. However, it is anticipated that a variety of different gases may be used.

Gas may flow through the filter assembly 20 from the inside-out. The filter assembly 20 may filter a gaseous mixture 14 through a variety of different methods, such as by first coalescing droplets of constituents of the mixture before separation from the remainder of the gaseous mixture. According to one embodiment, the filter assembly 20 may be a static or rotating crankcase ventilation system, a spin-on filter, or a compressed gas filter. The filter assembly 20 may be used within a variety of different applications, including but not limited to natural gas engines or compressed gas.

Although various configurations and components within the filter assembly 20 may be anticipated, the filter assembly 20 of FIGS. 1A-1D includes a filter housing 22 and a coalescing filter 30. The filter housing 22 houses, protects, and contains the coalescing filter 30. The top of the filter housing 22 is enclosed by a filter head or top endcap 24 and includes an inlet 10 for the unfiltered gaseous mixture 14 to enter into the filter housing 22 (and into the coalescing filter 30) and outlets 12 to allow clean or filtered gas to exit the filter housing 22. The bottom of the filter housing 22 includes a filter housing drain 26 that may be used to drain any liquid 18 accumulated at the bottom of the filter housing 22 during filtration.

The coalescing filter 30 may be used to filter a wet, unfiltered gaseous mixture 14 flowing through the filter assembly 20. The coalescing filter 30 includes a filter media 28, a nozzle assembly 50, an upper endplate 32, and a lower endplate 60. The filter media 28 is configured to filter a gas. The nozzle assembly 50 is configured to preclean the gaseous mixture before being filtered by the filter media 28 (as described further herein). The upper endplate 32 is configured to attach to and be positioned at an upper end of the filter media 28 and may be used for support. The lower endplate 60 is configured to attach to and be positioned at a lower end of the filter media 28 and may be used for support and/or drainage.

The filter precleaner or nozzle assembly 50 may preclean the unfiltered gaseous mixture 14 through a variety of different methods. For example, the nozzle assembly 50 may be an impactor precleaner. The nozzle assembly 50 may be or support a variety of types of impaction including variable impaction, as described further herein. The nozzle assembly 50 may separate out or remove a variety of different liquids and liquid particles from the unfiltered gaseous mixture 14, including aerosols, before the gaseous mixture 14 can flow through the filter media 28 for filtration. Accordingly, due to the nozzle assembly 50, the amount of liquid flowing through the filter media 28 may be minimized and the filter media 28 may remain dry, which preserves the integrity and life of the filter media 28. As described further herein, the nozzle assembly 50 includes a first nozzle plate 54, a second nozzle plate 254, and a tube 52.

According to the embodiment shown in FIGS. 1A-1D and 5, the unfiltered gaseous mixture 14 being filtered by the filter assembly 20 is directed through the inlet 10 of the filter assembly 20 (180), down the tube 52 of the nozzle assembly 50, and through a first nozzle plate 54 located on the tube 52 (182). The first nozzle plate 54 causes the unfiltered gaseous mixture 14 to impact the lower endplate 60 (and, optionally, a media patch 66 on the lower endplate 60) (184). Accordingly, the nozzle assembly 50 may separate the gaseous mixture 14 into gas 16 and liquid 18 by separating the liquid 18 from the gas 16. The liquid 18 is coalesced or isolated and is directed and drains or flows through at least one drain 64 proximate or coupled to the lower endplate 60 such that the liquid 18 drains through the lower endplate 60 (186), which prevents the liquid 18 from coming into to contact with the filter media 28, keeps the filter media 28 dry, and postpones or delays saturation of the filter media 28. Gas 16 may also flow through the drain 64 on the lower endplate 60. The gas 16 (without the liquid 18) is directed and flows separately through the filter media 28 for filtration and out through outlets 12 (188).

Figure 3A:
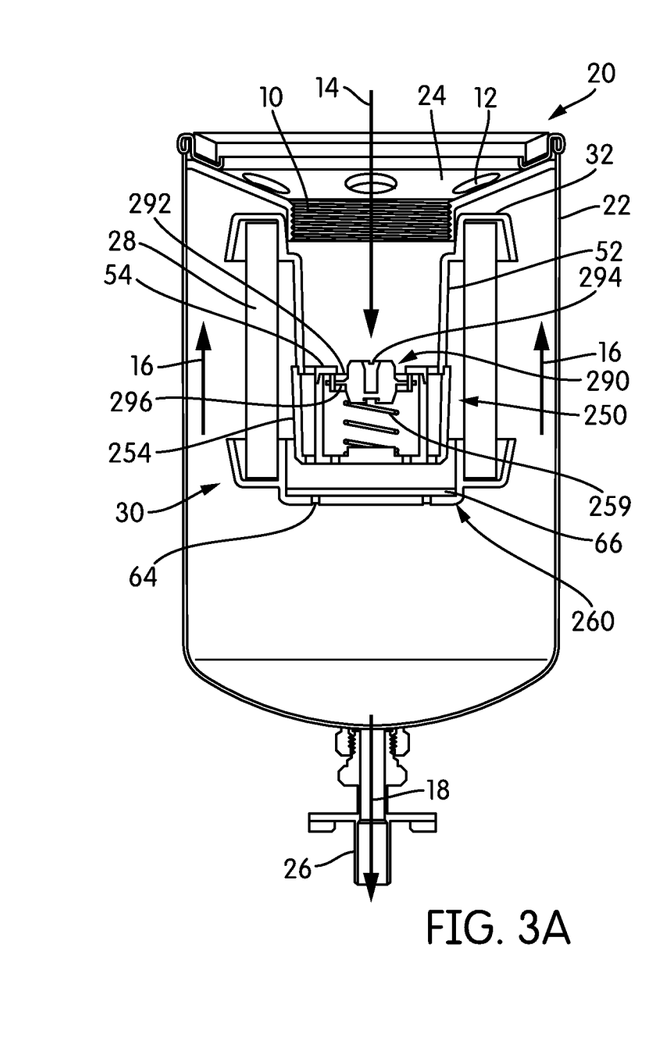
FIG. 3A is a cross-sectional view of a filter assembly according to still another embodiment.
Figure 3B:
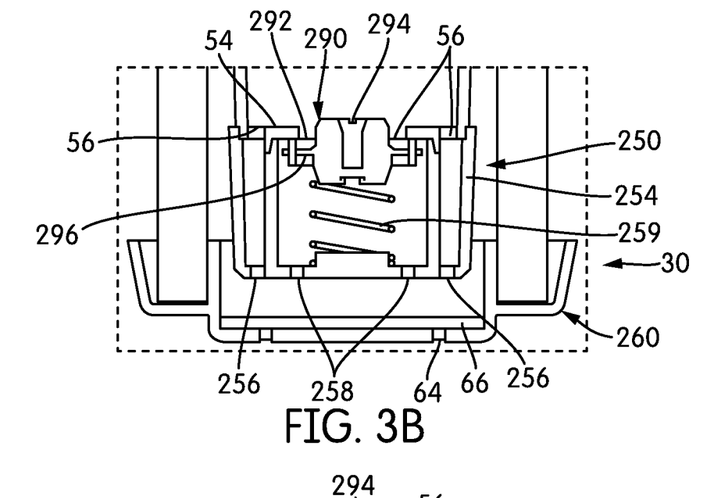
FIG. 3B is an enlarged, cross-sectional view of a portion of the filter assembly of FIG. 3A.
Figure 3C:
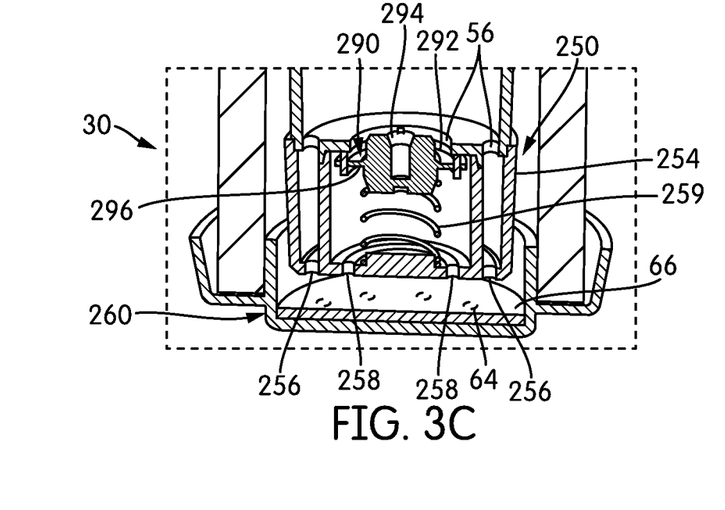
FIG. 3C is an enlarged, cross-sectional, perspective view of a portion of the filter assembly of FIG. 3A.

The lower endplate 60 (which is coupled to or is otherwise positioned proximate an end of the filter media 28), may be made out of a variety of different materials and constructed according to the desired configuration. For example, the top endcap 24, the upper endplate 32, and the lower endplate 60 may be made out of sheet metal and/or plastic (as shown in FIGS. 3A-3C).

The nozzle assembly 50 may be used and self-contained within conventional filter assemblies, according to one embodiment. In order to preclean the gas, the nozzle assembly 50 is positionable within the filter assembly 20, between the inlet 10 and the filter media 28 positioned within the filter housing 22 along a flow path through the filter housing 22. The various components of the nozzle assembly 50 may be integral with portions of the filter assembly 20 (e.g., the filter housing 22) or removable and reattachable from the portions of the filter assembly 20. The nozzle assembly 50 may optionally be modular and attach to various portions of the filter assembly 20.

Figure 1A:
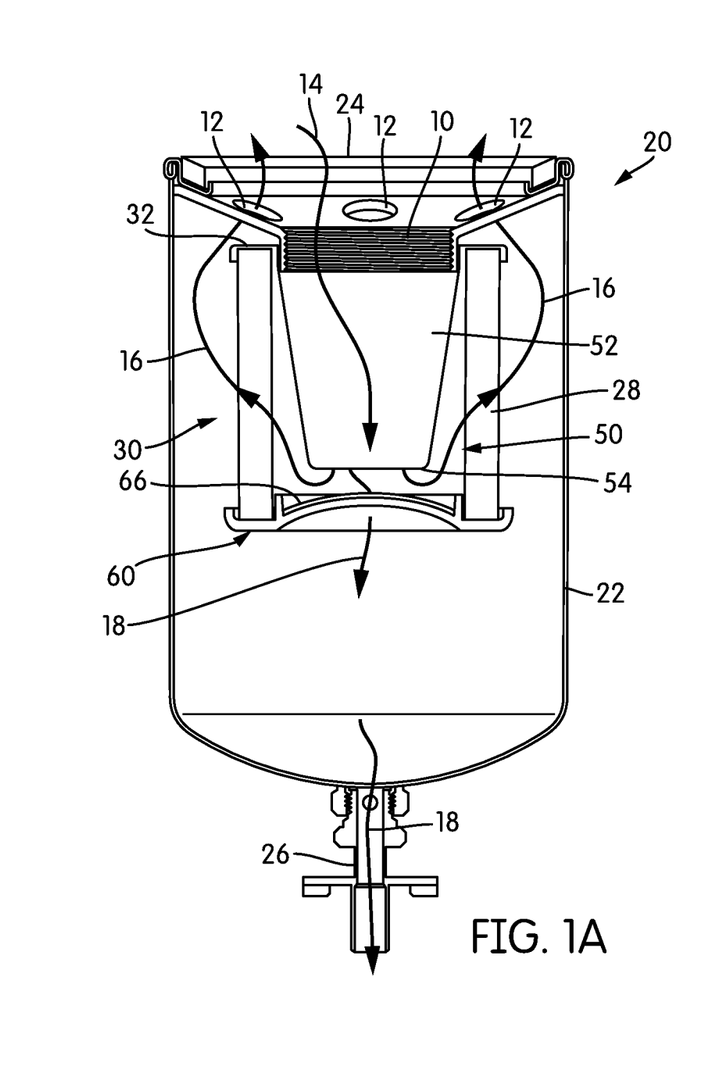
FIG. 1A is a cross-sectional view of a filter assembly according to one embodiment.
Figure 1B:
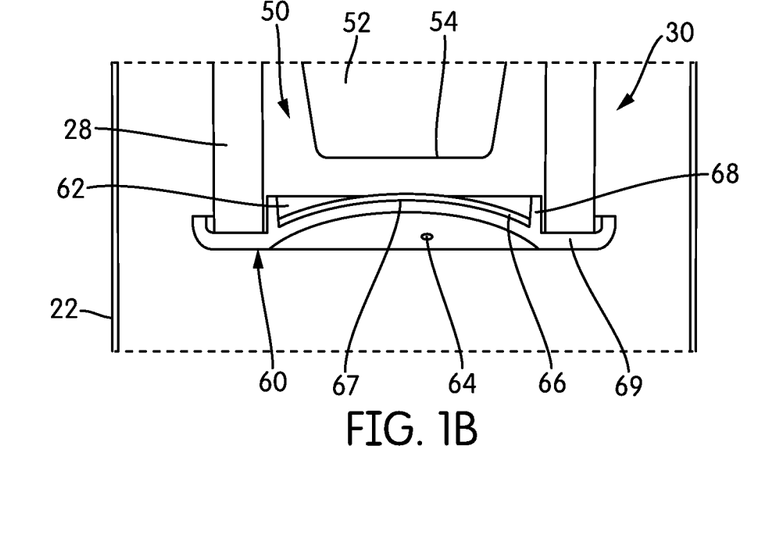
FIG. 1B is an enlarged, cross-sectional view of a portion of the filter assembly of FIG. 1A.
Figure 1C:
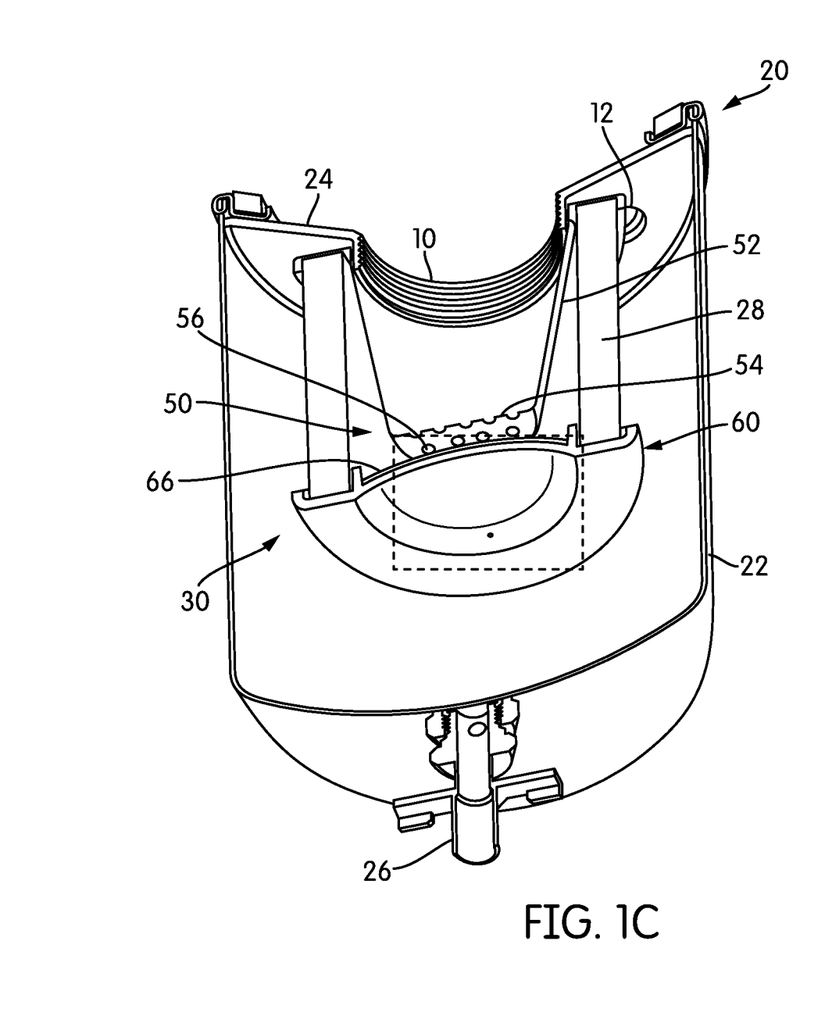
FIG. 1C is a bottom perspective, cross-sectional view of the filter assembly of FIG. 1A.

As shown in FIG. 1A, the nozzle assembly 50 may also comprise the impactor or entry center tube 52. The unfiltered gaseous mixture 14 flows through the tube 52 of the nozzle assembly 50. The tube 52 is positionable within the filter assembly 20 downstream of the inlet 10. The tube 52 directs the flow of the unfiltered gaseous mixture 14 downward toward the bottom of the filter housing 22 (i.e., toward the first nozzle plate 54) and is positioned upstream of the filter media 28 within the filter assembly 20. Allowing the tube 52 to be contained within the filter assembly 20 significantly reduces the service clearance to remove and replace the filter assembly 20. The tube 52 may comprise a standpipe within the filter assembly 20 or attachable to a portion of the filter assembly 20.

The tube 52 may optionally be attached to the top endcap 24, the upper endplate 32, or to the filter media 28. According to one embodiment, the tube 52 may optionally be removable and replaceable with each filter servicing event. For example, the tube 52 may include threads to screw on and off of the top endcap 24, the upper endplate 32, and/or the filter media 28 (and the top endcap 24, the upper endplate 32, and/or the filter media 28 may have complementary threads to attach with the tube 52). As a further example, the tube 52 may be integral with the upper endplate 32 (which is attached to the filter media 28 and the filter media 28 is attached to the lower endplate 60). Therefore, the tube 52 may attach the nozzle assembly 50, the upper endplate 32, the filter media 28, and the lower endplate 60 together to the top endcap 24 of the filter housing 22.

According to another embodiment, the tube 52 may be a permanent part of or integral with a portion of the filter assembly 20. Accordingly, the tube 52 may be permanently attached to or integral with the top endcap 24, the upper endplate 32, and/or the filter media 28.

According to one embodiment, the tube 52 may have a proximal end and a distal end. The proximal end may be upstream of the distal end. According to one embodiment, the proximal end of the tube 52 may be attachable to a portion of the filter assembly 20, such as the inlet 10, the top endcap 24, a top portion of the filter media 28, or the upper endplate 32. According to another embodiment, the proximal end of the tube 52 may be integral with the upper endplate 32 such that the tube 52 and the upper endplate 32 are one piece with each other and cannot be separated from each other. The tube 52 may be one piece or may include separate attachable pieces.

Figure 4:
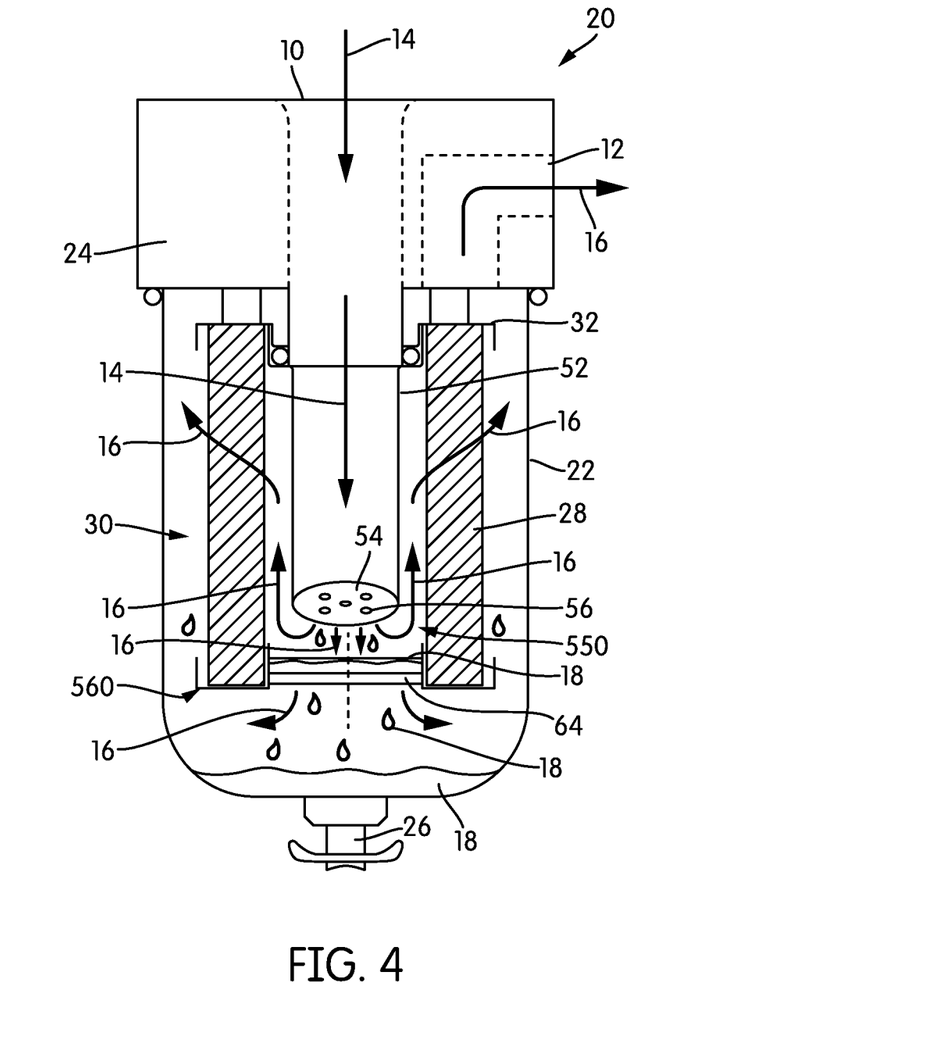
FIG. 4 is a cross-sectional view of a filter assembly according to another embodiment.
Figure 5:
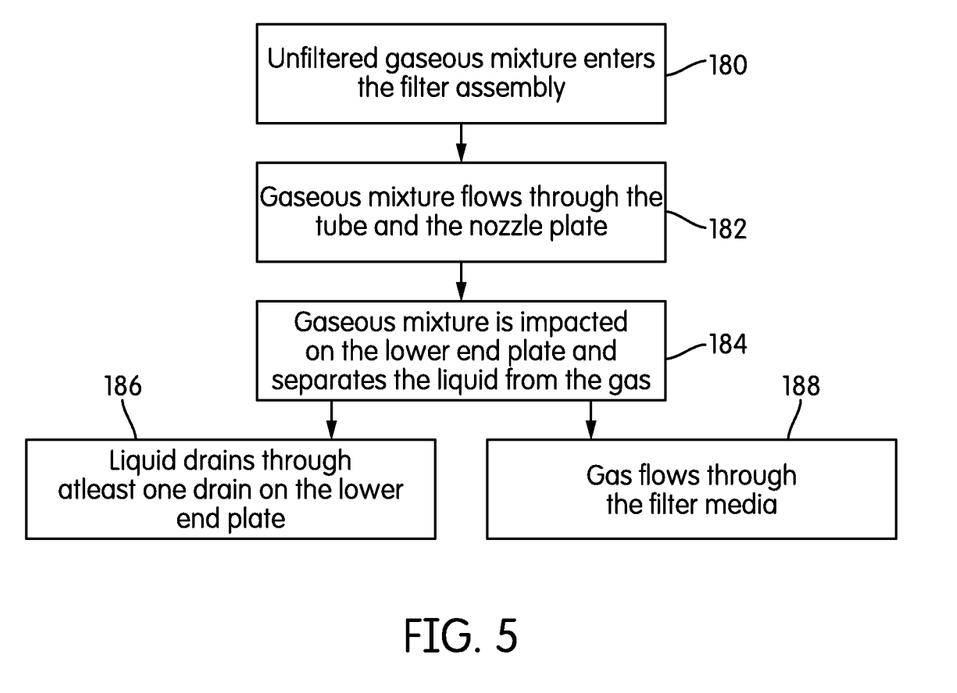
FIG. 5 is a schematic view of filtration within a filter assembly according to one embodiment.

The tube 52 may have a conical shape and fit within a center area of the filter media 28. According to one embodiment, the tube 52 may have a frustoconical shape such that the side walls of the tube 52 are angled relative to a vertical axis extending through the filter media 28 and converge inward toward one of the proximal end or the distal end of the tube 52. Accordingly, the diameter of the proximal end and the diameter of the distal end of the tube 52 may be different. As shown in FIG. 1A, the diameter of the proximal end is larger than the diameter of the distal end of the tube 52, thereby directing the gaseous mixture 14 toward the center region (e.g., the impaction area 67) of the lower endplate 60. According to another embodiment as shown in FIGS. 3A and 4, the diameter of the proximal end and the diameter of the distal end of the tube 52 may be approximately the same.

Figure 2A:
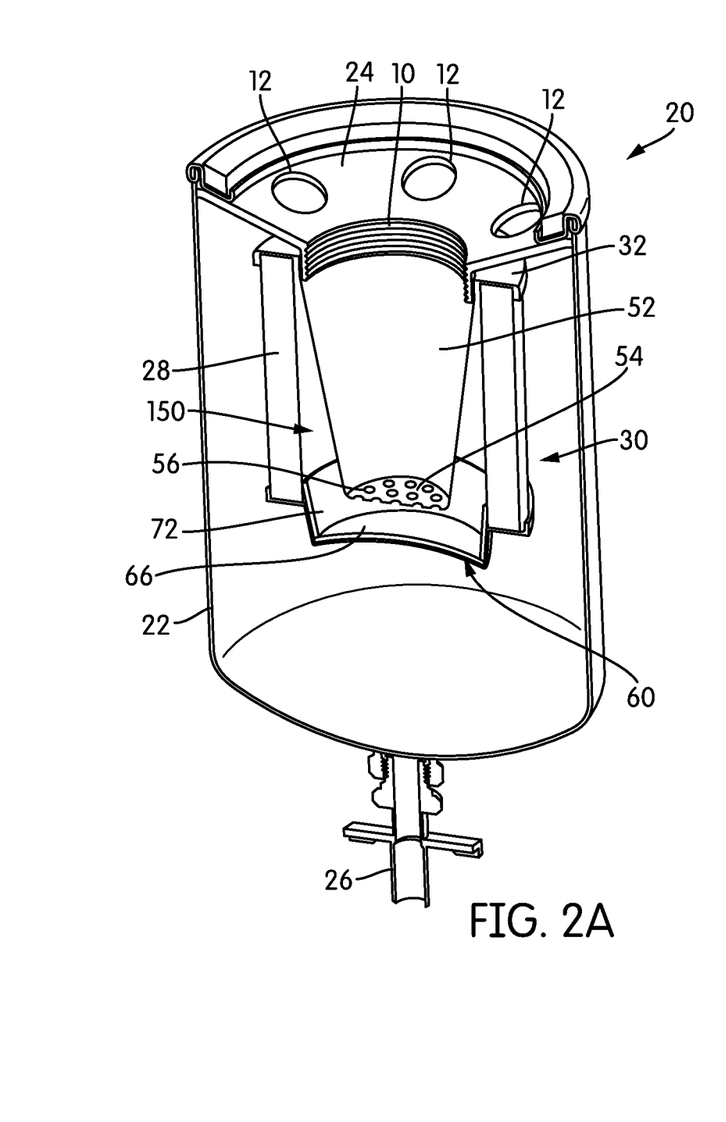
FIG. 2A is a top perspective, cross-sectional view of a filter assembly according to another embodiment.
Figure 2B:
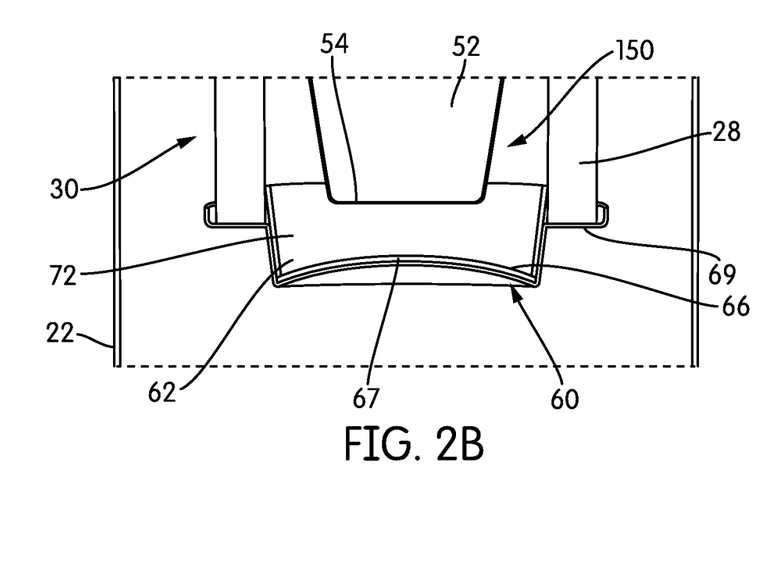
FIG. 2B is an enlarged, cross-sectional view of a portion of the filter assembly of FIG. 2A.
Figure 2C:
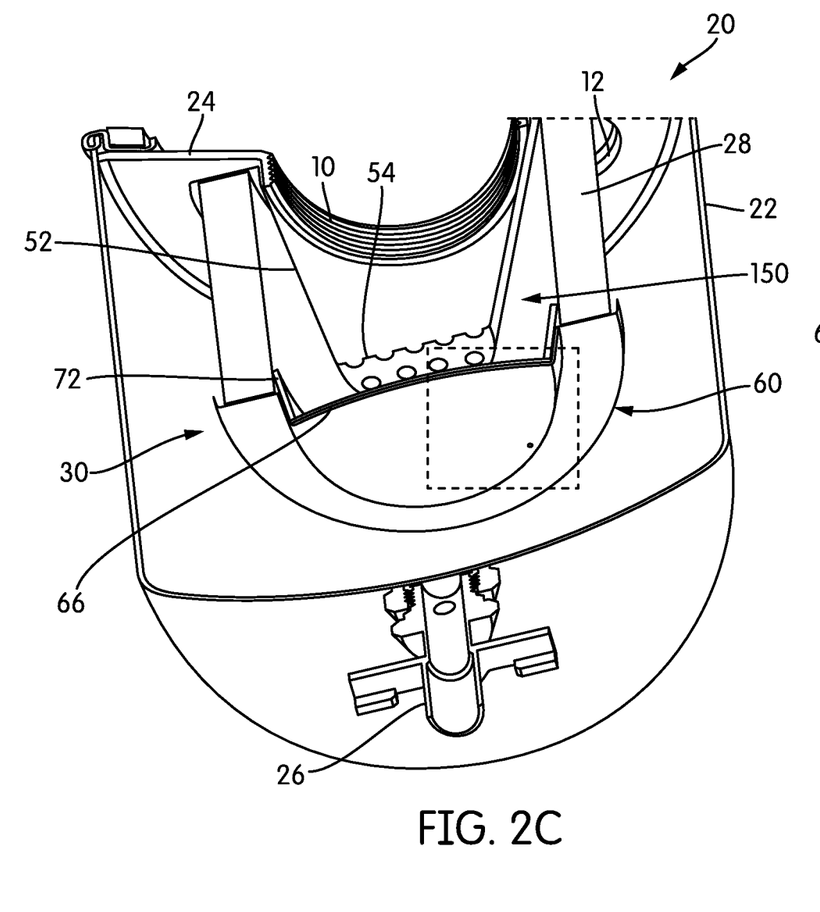
FIG. 2C is a bottom perspective, cross-sectional view of the filter assembly of FIG. 2A.

The first nozzle plate 54 may be attached or mounted to the bottom or distal end of the tube 52 (which is upstream of the filter media 28). The first nozzle plate 54 may help direct and funnel the unfiltered gaseous mixture 14 toward a lower endplate 60 in a lower region within the filter assembly 20. The first nozzle plate 54 may optionally be integral with the tube 52 or removeable and/or reattachable from the tube 52. As shown, for example, in FIGS. 1C and 2A, the first nozzle plate 54 may include at least one impactor opening 56 to direct or funnel the gaseous mixture 14 downward to an impaction area 67 on the lower endplate 60. The first nozzle plate 54 may be attached to the tube 52 through a variety of different mechanisms, including but not limited to adherents (e.g., glue), welding (e.g., ultrasonic or spin welding (as shown, for example, in FIGS. 3A-3C)), a frictional fit, screws, hooks, clamps, clips, or snaps or the first nozzle plate 54 may be screwed onto the tube 52.

The upper endcap or upper endplate 32 is positioned at or attached directly or indirectly to an upper end of the filter media 28 above the first nozzle plate 54. The upper endplate 32 and the tube 52 are attached to each other (and the first nozzle plate 54 is attached to the tube 52) such that the tube 52 is upstream of the first nozzle plate 54.

The lower or bottom endcap or endplate 60 is positioned at or attached directly or indirectly to a lower end of the filter media 28 beneath the first nozzle plate 54. Accordingly, the lower endplate 60 may include an impaction area 67 (as described further herein) and a filter media holder 69. The impaction area 67 and the filter media holder 69 may be fluidically separated by a wall or divider 68 or a ring 72 (as described further herein). Accordingly, the filter media holder 69 and the divider 68 (and/or the ring 72) may surround or encircle the impaction area 67.

The filter media holder 69 is configured to hold or secure the filter media 28 such that the lower endplate 60 and the filter media 28 are securely attached to each other. The filter media holder 69 may be attached to the bottom portion or lower end of the filter media 28 with a variety of different mechanisms, including but not limited to adherents (e.g., glue), welding (e.g., ultrasonic or spin welding), potting or embedding (as shown, for example, in FIGS. 3A-3C), a frictional fit, screws, hooks, clamps, clips, or snaps.

The lower endplate 60 may be shaped in different configurations, according to the desired functionality. For example, the lower endplate 60 may be curved or flat and hard or resilient. According to one embodiment as shown in FIGS. 1A-1D, the lower endplate 60 may be curved upward in a middle portion (e.g., the impaction area 67), thus creating a lowered annular dam or area 62 surrounding the middle portion within the periphery of the divider 68 or the ring 72.

The impaction surface, zone, or area 67 may be a top surface of the lower endplate 60 that is directly beneath the first nozzle plate 54. The impaction area 67 may provide a surface for the unfiltered gaseous mixture 14 to impact to filter the liquid 18 out of the gaseous mixture 14. Accordingly, the gaseous mixture 14 may hit the impaction area 67 and the liquid 18 may at least partially adhere to the impaction area 67.

In order to further isolate the collected liquid 18 from the filter media 28 as the liquid 18 is draining through the lower endplate 60, the lower endplate 60 may be configured such that a pool of the liquid 18 is collected on or within the lower endplate 60 in the lowered annular area 62. For example, the lower endplate 60 may form an annular pool of liquid 18 in the lowered annular area 62 that is separated from the filter media 28, as shown in FIGS. 1A-1D. The lowered annular area 62 collects the liquid 18 from the gaseous mixture 14 and isolates the liquid 18 from the filter media 28. The lowered annular area 62 optionally surrounds the impaction area 67 of the lower endplate 60 and the filter media holder 69 and the divider 68 (and/or the ring 72) optionally surrounds or encircles the lowered annular area 62. Accordingly, liquids that are slow to drain through the lower endplate 60 may collect, reside, or pool within the lowered annular area 62 without coming into contact with the filter media 28, thus keeping the filter media 28 dry.

The lower endplate 60 allows the liquid 18 to flow or drain completely through the lower endplate. Accordingly, the lower endplate 60 may be either porous or non-porous with one or a collection of openings or drains 64. The lower endplate 60 may not require any additional provisions or components in order to allow the liquid to drain through the lower endplate 60.

Figure 1D:
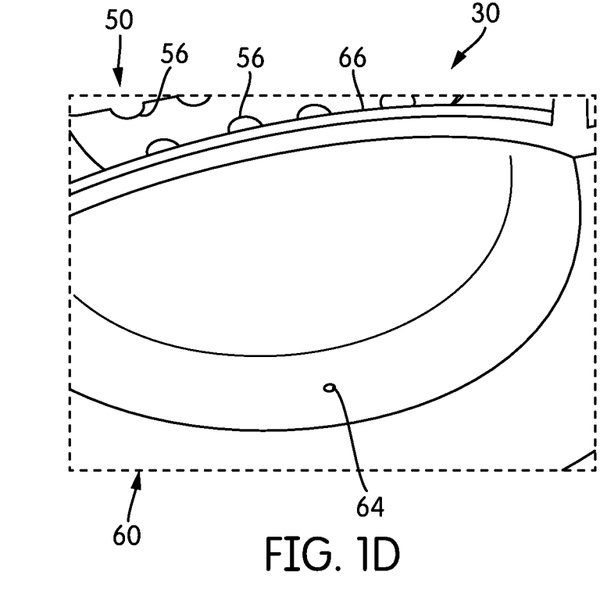
FIG. 1D is an enlarged view of a section of the filter assembly of FIG. 1C.
Figure 2D:
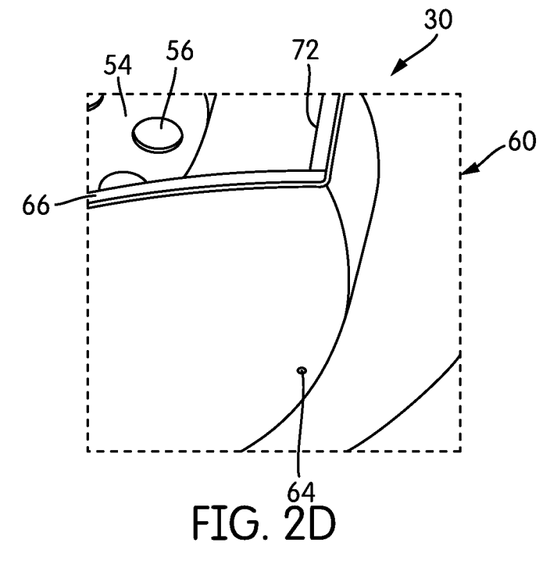
FIG. 2D is an enlarged view of a section of the filter assembly of FIG. 2C.

For example, according to the embodiment shown in FIGS. 1A-1D, the lower endplate 60 includes an internal weep opening or drain 64 to allow liquid 18 to flow through the lower endplate 60. As shown in FIGS. 1D and 2D, the drain 64 is an opening that extends substantially vertically through the lower endplate 60 and functions as a drain channel for any collected liquid 18. However, it is also anticipated that the drain 64 may extend substantially horizontally or at an angle through the lower endplate 60. The drain 64 is isolated from the filter media 28 in order to help keep the filter media 28 dry for a longer period of time.

The drain 64 may be a single opening or multiple openings in the bottom of the lower endplate 60, depending on the desired configuration (e.g., drainage speed and location). The drains 64 may be located in different areas along the lower endplate 60. For example, the drain 64 may be located in the impaction area 67 or along the periphery of the impaction area 67 (e.g., in the lowered annular area 62). The drain 64 may be a variety of different sizes in order to allow the liquid 18 to drain through the lower endplate 60, while allowing minimal bypass for the gas to flow around the filter media 28. According to one embodiment, the diameter of the drain 64 may be between 0.1 and 1 mm. According to another embodiment, the diameter of the drain 64 may be between 0.25 and 0.75 mm. According to yet another embodiment, the diameter of the drain 64 may be approximately 0.5 mm.

According to another embodiment as shown in FIG. 4, the lower endplate 560 may be a porous or sintered disc or a fibrous mat to allow the liquid 18 to flow and filter through the lower endplate 560 (alternative or in addition to openings or drains 64 for drainage). All of the lower endplate 560 may be sintered or certain portion of the lower endplate 560 may be sintered depending on the desired drainage. As shown in FIG. 4, after flowing through the nozzle assembly 550, the liquid 18 from the gaseous mixture 14 can accumulate on top of the lower endplate 560 and beneath of the lower endplate 560 (e.g., on the filter housing 22) without coming in contact with the filter media 28.

According to one embodiment, the lower endplate 60 may filter any gas 16 that flows through the lower endplate 60 instead of the filter media 28, which may further prevent or deter the gas 16 from bypassing the filter media 28. According to one embodiment as shown in FIGS. 1A-1D, impaction media, filtration media, fibrous mat or pad, or a media patch 66 is positioned along the drain 64 on the lower endplate 60 such that the media patch 66 covers the drain 64 to filter any gas 16 flowing through the lower endplate 60. The media patch 66 may have similar and/or more efficient filtering capabilities as the filter media 28. Accordingly, according to one embodiment, gas 16 that flows through the lower endplate 60 is filtered. The gas 16 flowing through the lower endplate 60 may optionally be filtered to the same extent as or more efficiently than the gas 16 that flows through the filter media 28. The media patch 66 may capable of impaction and/or coalescing. The media patch 66 may prevent the drain 64 from being directly connected to the clean and dirty sides within the filter assembly 20, resulting in less carry-over of potential contaminants. According to another embodiment, the gas 16 that flows through the lower endplate 60 may not be filtered.

The media patch 66 may comprise, for example, a fibrous media bed or a porous disc that at least covers a drainage area of the lower endplate 60 (e.g., the drain 64, a portion of the lower endplate 60, or the entire lower endplate 60). The media patch 66 may optionally be replaceable in order to provide a clean filter within filter assembly 20 after use. Although the media patch 66 is shown on top of the lower endplate 60 and the drain 64, it is anticipated that the media patch 66 may be positioned beneath the lower endplate 60 and the drain 64.

Alternatively or additionally, the lower endplate 60 may inherently filter any gas 16 flowing through the lower endplate 60 if the lower endplate 60 is, for example, sintered (as shown in FIG. 4).

The media patch 66 may be attached to the top or bottom of the lower endplate 60 through a variety of different methods. As shown in FIGS. 1A-1D and 3A-3C, the media patch 66 or 466 may be ultrasonic or spin welded or glued to the lower endplate 60, 260, or 460.

According to another embodiment as shown in FIGS. 2A-2D, the media patch 66 may be held in place on the lower endplate 60 by a structure, such as a ring 72 or stake. The ring 72 extends in a circle on the lower endplate 60 and is positioned radially between the impaction area 67 and the filter media holder 69. According to one embodiment, the ring 72 extends along the inner circumference of the filter media 28 (and therefore extends vertically above the lower endplate 60), thus keeping any residual liquid 18 (that has not been drained through the lower endplate 60 yet) separate from the filter media 28.

The ring 72 may be a variety of different sizes, according to the desired configuration. For example, the ring 72 may extend vertically above the top of the lower endplate 60 by 0 to 20 mm. According to one embodiment, the ring 72 may extend vertically above the lower endplate 60 by 1 to 5 mm. According to another embodiment, the ring 72 may extend vertically above the lower endplate 60 by 2 to 4 mm. According to yet another embodiment, the ring 72 may extend vertically above the lower endplate 60 by approximately 3 mm.

According to another embodiment as shown in FIGS. 3A-3C, the nozzle assembly 250 uses a combination of static and variable impaction for with a broad range of filtering applications, in particular wider flow rates. Accordingly, the nozzle assembly 250 includes a static impactor and a variable impactor 290, as describe further herein. The static impactor may be used primarily for a low or medium flow rate to increase efficiency and may also lower the pressure drop across the nozzle assembly 250. The variable impactor 290 may be used for a higher flow rate.

In the nozzle assembly 250, the tube 52 includes the first nozzle plate 54 with at least one opening 56 to direct the gaseous mixture 14 toward a second nozzle plate 254. The second nozzle plate 254 attaches to the distal end of the tube 52 through a variety of different mechanisms (similar to the first nozzle plate 54, as described further herein) beneath the openings 56 of the first nozzle plate 54 and includes fixed or static impactor nozzles or openings 256 and variable impactor nozzles or openings 258. The various openings 56 on the first nozzle plate 54 direct the gaseous mixture 14 toward either the variable impactor openings 258 or the static impactor openings 256. For static impaction, the gaseous mixture 14 flows through openings 56 that lead directly to the static impactors openings 256. For variable impaction, the gaseous mixture 14 flows through openings 56 that lead to the variable impactor 290 to the variable impactor openings 258.

The variable impactor 290 may be positioned between the openings 56 on the first nozzle plate 54 and the variable impactor openings 258 on the second nozzle plate 254. The variable impactor 290 includes a spring plate 296 with a circumferential seal 292 and a biasing member or spring 259. The spring plate 296 is moved by the spring 259 and is positioned on top of the spring 259 and below the first nozzle plate 54. The spring plate 296 is configured to seal to the first nozzle plate 54 under low fluid pressure. The spring plate 296 may optionally include a central aperture 294 to allow fluid to flow through the spring plate 296, regardless of the fluid pressure (e.g., static impaction).

The nozzle assembly 250 may support a variation in the fluid flow. For example, the variable impactor 290 either restricts or allows the fluid to flow depending on the rate of fluid input or pressure. Under a low fluid pressure, the spring 259 may remain expanded, which may press and seal the spring plate 296 (and thus the seal 292) against the first nozzle plate 54 and prevent the gaseous mixture 14 from flowing through certain portions of the tube 52 (e.g., around the perimeter of the spring plate 296). The gaseous mixture 14 can still flow through the other impactor holes or openings 56 to the static impactor openings 256 and/or the center aperture 294 of the spring plate 296 for static impaction. Under a high fluid pressure, the fluid compresses the spring 259, which may release or separate the spring plate 296 (and thus the seal 292) from the first nozzle plate 54. This allows the gaseous mixture 14 to flow around the perimeter of the spring plate 296 such that more fluid flows through the variable impactor openings 258 (and thus fluid flows through both the static impactor openings 256 and the variable impactor openings 258 to the lower endplate 260).

It is anticipated that the various components, configurations, and features of the different embodiments of the nozzle assembly and lower endplate may be combined according to the desired use and configuration.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

The terms "coupled," "connected," and the like as used herein mean the joining of two members directly or indirectly to one another. Such joining may be stationary (e.g., permanent) or moveable (e.g., removable or releasable).

Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "upper," "lower," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. Additionally, it should also be understood that features disclosed in different embodiments may be combined into yet further embodiments not necessarily depicted or described herein. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A coalescing filter comprising:
    a filter media;
    a nozzle assembly for precleaning an unfiltered gaseous mixture, the nozzle assembly comprising a first nozzle plate positioned upstream of the filter media; and
    a lower endplate attached to and positioned at a lower end of the filter media beneath the first nozzle plate, the lower endplate allowing liquid to drain through the lower endplate;
    wherein the unfiltered gaseous mixture impacts the lower endplate such that liquid from the unfiltered gaseous mixture flows through the lower endplate and gas from the unfiltered gaseous mixture flows through the filter media.

2. The coalescing filter of claim 1, wherein the nozzle assembly further comprises a tube comprising a proximal end and a distal end, the distal end attached to the first nozzle plate, the proximal end attached to an upper endplate positioned at an upper end of the filter media such that the tube is upstream of the first nozzle plate.

3. The coalescing filter of claim 2, wherein the tube directs the unfiltered gaseous mixture toward the first nozzle plate, and the first nozzle plate directs the unfiltered gaseous mixture toward the lower endplate.

4. The coalescing filter of claim 1, wherein the first nozzle plate comprises at least one impactor opening, the at least one impactor opening directing the unfiltered gaseous mixture toward an impaction area of the lower endplate such that the unfiltered gaseous mixture impacts the impaction area.

5. The coalescing filter of claim 1, wherein the lower endplate comprises an impaction area and a filter media holder, and wherein the impaction area and the filter media holder are liquidly separated by a divider.

6. The coalescing filter of claim 5, wherein the filter media holder and the divider encircle the impaction area.

7. The coalescing filter of claim 5, wherein the lower endplate is curved upward in the impaction area such that the lower endplate has a lowered annular area surrounding the impaction area, the lowered annular area collecting the liquid from the unfiltered gaseous mixture, and wherein the filter media and the divider encircle the lowered annular area.

8. The coalescing filter of claim 5, further comprising a ring positioned on the lower endplate, the ring positioned radially between the impaction area and the filter media holder.

9. The coalescing filter of claim 8, wherein the ring extends along an inner circumference of the filter media and vertically above the lower endplate.

10. The coalescing filter of claim 1, wherein the nozzle assembly further comprises a second nozzle plate positioned downstream of the first nozzle plate, the second nozzle plate comprising at least one static impactor opening, at least one variable impactor opening, and a variable impactor leading to the at least one variable opening.

11. The coalescing filter of claim 10, wherein the variable impactor comprises a spring plate and a spring such that the spring plate seals with at least a portion of the first nozzle plate under low fluid pressure and separates from the first nozzle plate under high fluid pressure.

12. The coalescing filter of claim 1, further comprising a media patch positioned on the lower endplate and configured to filter the gas.

13. The coalescing filter of claim 12, wherein the media patch covers a drain that extends through the lower endplate.

14. The coalescing filter of claim 1, wherein the lower endplate is one of porous or sintered.

15. The coalescing filter of claim 1, further comprising a drain extending through the lower endplate.

16. The coalescing filter of claim 15, wherein the drain allows the liquid from the unfiltered gaseous mixture to flow through the lower endplate.

17. The coalescing filter of claim 1, wherein the lower endplate comprises a lowered annular area configured to collect liquid and isolate the liquid from the filter media.

18. A filter assembly comprising:
    a filter housing; and
    a coalescing filter positioned within the filter housing, the coalescing filter comprising
        a filter media,
        a nozzle assembly for precleaning an unfiltered gaseous mixture, the nozzle assembly comprising a first nozzle plate positioned upstream of the filter media, and
        a lower endplate attached to and positioned at a lower end of the filter media beneath the first nozzle plate, the lower endplate allowing liquid to drain through the lower endplate,
        wherein the unfiltered gaseous mixture impacts the lower endplate such that liquid from the unfiltered gaseous mixture flows through the lower endplate and gas from the unfiltered gaseous mixture flows through the filter media.

19. The filter assembly of claim 18, wherein the nozzle assembly further comprises a tube comprising a proximal end and a distal end, the distal end attached to the first nozzle plate, the proximal end attached to an upper endplate positioned at an upper end of the filter media such that the tube is upstream of the first nozzle plate.

20. The filter assembly of claim 18, further comprising a drain extending through the lower endplate.

21. The filter assembly of claim 18, wherein the lower endplate comprises a lowered annular area configured to collect liquid and isolate the liquid from the filter media.

22. A method of precleaning an unfiltered gaseous mixture comprising:

directing the unfiltered gaseous mixture into a filter assembly;

directing the unfiltered gaseous mixture through a first nozzle plate of a nozzle assembly of the filter assembly, the first nozzle plate positioned upstream of a filter media;

impacting the unfiltered gaseous mixture on a lower endplate, the lower endplate attached to and positioned at a lower end of the filter media beneath the first nozzle plate; and draining liquid from the unfiltered gaseous mixture through the lower endplate, wherein gas from the unfiltered gaseous mixture flows through the filter media.

23. The method of claim 22, wherein the unfiltered gaseous mixture flows through a tube of the nozzle assembly, the tube comprising a proximal end and a distal end, the distal end attached to the first nozzle plate, the proximal end attached to an upper endplate positioned at an upper end of the filter media such that the tube is upstream of the first nozzle plate.

24. The method of claim 22, wherein the liquid drains through a drain extending through the lower endplate.

25. The method of claim 22, wherein the liquid collects on a lowered annular area of the lower endplate such that the liquid is isolated from the filter media.

\* \* \* \* \*